United States Patent
Harrold et al.

(10) Patent No.: US 6,487,909 B2
(45) Date of Patent: Dec. 3, 2002

(54) ACOUSTIC WAVEGUIDE SENSING THE CONDITION OF COMPONENTS WITHIN GAS TURBINES

(75) Inventors: Ronald Thomas Harrold, Murrysville, PA (US); Zal N. Sanjana, Pittsburgh, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 0 days.

(21) Appl. No.: 09/776,818

(22) Filed: Feb. 5, 2001

(65) Prior Publication Data

US 2002/0157471 A1 Oct. 31, 2002

(51) Int. Cl.$^7$ ............................................. G01N 29/00
(52) U.S. Cl. .......................... 73/593; 600/602; 600/660
(58) Field of Search ...................... 73/593, 660, 587, 73/598, 599, 600, 602, 645

(56) References Cited

U.S. PATENT DOCUMENTS

| | | | | |
|---|---|---|---|---|
| 3,940,952 A | * | 3/1976 | Mitchell et al. | 73/629 |
| 4,372,163 A | * | 2/1983 | Tittmann et al. | 73/602 |
| 4,524,622 A | * | 6/1985 | Suzuki et al. | 73/602 |
| 4,537,630 A | * | 8/1985 | Syed | 73/589 |
| 4,545,250 A | * | 10/1985 | Miwa | 73/602 |
| 4,603,584 A | * | 8/1986 | Bartle et al. | 73/599 |
| 4,619,143 A | * | 10/1986 | Franken | 73/598 |
| 4,685,335 A | | 8/1987 | Sato et al. | 73/660 |
| 4,696,191 A | * | 9/1987 | Claytor et al. | 73/600 |
| 5,005,417 A | * | 4/1991 | Kawasaki et al. | 73/593 |
| 5,024,093 A | | 6/1991 | Sasaki et al. | 73/633 |
| 5,070,722 A | | 12/1991 | Hawman et al. | 73/28.01 |
| 5,152,172 A | | 10/1992 | Leon et al. | 73/579 |
| 5,195,046 A | * | 3/1993 | Gerardi et al. | 73/583 |
| 5,349,443 A | * | 9/1994 | Guerra | 356/376 |
| 5,445,027 A | | 8/1995 | Zorner | 73/593 |
| 5,670,879 A | * | 9/1997 | Zombo et al. | 73/660 |
| 5,894,092 A | * | 4/1999 | Lindgren et al. | 73/598 |
| 5,942,690 A | | 8/1999 | Shvetsky | 73/660 |

OTHER PUBLICATIONS

R.T. Harrold and Z.N. Sanjana, "Acoustic waveguide embedded sensors for submarine structures",ADPA/AIAA/ASME/SPIE Conference on Active Materials and Adaptive Structures, (Nov. 4–8, 1991) Alexandria, VA.

* cited by examiner

Primary Examiner—Hezron Williams
Assistant Examiner—Jacques Saint-Surin (57) ABSTRACT

A system for online monitoring the condition of a thermal barrier coating on the vanes and/or blades of a combustion turbine, or other forms of component deterioration affecting the acoustic properties of the vanes and/or blades. The system begins with a signal generator for transmitting a signal to an acoustic transmitter, and then to an acoustic waveguide secured within the turbine, adjacent to a vane. Acoustic waves passing through the vane's coating will have a certain magnitude and velocity when passing through an intact coating, which will change as the coating deteriorates. Additional variation of the acoustic wave will occur due to pressure pulses from passing blades, with the magnitude of the pressure pulses increasing as the blade's coating deteriorates. The acoustic waves are then received by a second acoustic waveguide. The resulting signal will be converted from an acoustic signal to an electrical signal by an acoustic receiver, and will pass through a filter to remove the lower frequency signals of the turbine from the higher frequency signals to be analyzed. The remaining higher frequency signals are sent to a computer, permitting the variations in the acoustic waves to be analyzed. A second embodiment relies solely on pressure pulses from passing blades to generate acoustic signals within the vanes.

6 Claims, 6 Drawing Sheets

ACOUSTIC WAVEGUIDE SENSING THE CONDITION OF COMPONENTS WITHIN GAS TURBINES

BACKGROUND OF THE INVENTION

1. Field of the Invention

The invention relates to online monitoring of combustion turbines for defects. More specifically, the invention is an apparatus and method for using acoustic signals to monitor the condition of combustion turbine component online.

2. Background Information

Combustion turbines typically operate at extremely high temperatures, for example, 2500° F. to 2900° F. (1371° C. to 1593° C.). Such high temperatures will cause failure of various components unless they are protected from the heat. These components include the rotating blades of the turbine, and the vanes for directing gas flow within the turbine. A typical combustion turbine will have three to four rows each of blades and vanes, with approximately 50 to 100 blades or vanes per row, and will typically have approximately 500 total blades and vanes to protect. A commonly used material for vanes and blades is nickel-cobalt. These components are usually insulated by a thermal barrier coating to enable their use within high temperature environments. A typical thermal barrier coating is yttria-zirconia.

Currently, it is necessary to periodically stop the turbine and inspect the components for deterioration of the thermal barrier coating, defects in other coatings, or other defects, for example, formation of cracks. It would be desirable to monitor the condition of these components while the turbine is in use. Avoiding the need to periodically stop the turbine for inspection reduces downtime, increasing the turbine's efficiency. Similarly, early detection of defects reduces repair costs and outage time, again increasing turbine efficiency. A need exists for providing earlier detection of defects, and a means of locating the defect, simplifying the inspection and repair procedure once a defect is identified.

One proposed system for detecting and locating defects within turbine components is described in U.S. Pat. No. 5,445,027 issued to W. Zörner on Aug. 29, 1995. The system involves using a probe on the housing of the turbine to measure the acoustic spectrum of the turbine. This acoustic spectrum is then compared with a reference spectrum, with deviations from this reference spectrum indicating a damaged turbine blade. A preferred embodiment of this method includes generating an acoustic signal to increase the intensity of the acoustic spectrum within the turbine.

U.S. Pat. No. 5,942,690 issued to A. Shvetsky on Aug. 24, 1999, describes an apparatus and method for ultrasonic inspection of rotating machinery while the machinery is in operation. The method uses an ultrasonic transducer to radiate pulses of ultrasonic energy at a frequency substantially equal to a subharmonic of the frequency of the turbine rotation. The transducer will sense reflections of the ultrasonic pulses from the blade, and convert the reflections into an electrical signal. Changes in the reflected signal can indicate a damaged blade. If this apparatus and method were used with a combustion turbine, it would be difficult to precisely direct an acoustic wave through the high pressure, flowing gas present within the turbine.

Accordingly, there is a need to provide an online monitor for identifying the onset of a change in the condition of combustion turbine components. Additionally, there is a need identify the general location of the defect. Further, there is a need to detect the inception of defects within a coating protecting these components.

SUMMARY OF THE INVENTION

The invention is a system for monitoring the condition of a component within a combustion turbine during operation of the turbine, and in its preferred form can be used to monitor the thermal barrier coating on the blades and vanes within the turbine. The system relies on detecting changes in the magnitude and/or velocity of acoustic waves created by gas pressure exerted on the vanes (for directing gas flow) and blades (for converting the gas pressure into work).

As the combustion turbine is operated, a pulse signal generator will generate a signal to an acoustic transmitter, which will convert the electrical signal to an acoustic wave for transmittal through a high frequency acoustic waveguide to each vane. Acoustic waves passing through each vane are received by a second acoustic waveguide. An acoustic waveguide receiver will transmit a signal corresponding to the acoustic waves received to an acoustic receiver for conversion of the acoustic signal to an electrical signal. The signal is then transmitted to a filter to remove the lower frequency signals of the turbine from the higher frequency signals to be analyzed. The signal is finally sent to a storage scope and/or computer, permitting the variations in the acoustic waves to be analyzed.

If only monitoring the condition of the vanes, a pulsed acoustic signal may be sent through the vanes. The resulting acoustic wave will have a certain magnitude and velocity when passing through a vane with an intact coating. The magnitude and velocity of the acoustic wave will vary according to the condition and bond strength of the thermal barrier coating, and the strain to which the vane is subjected. As the coating on the vane deteriorates, the magnitude and/or velocity of the resulting acoustic wave will change, indicating that a vane needs servicing.

A rapid sequence of pulses, approximating a steady acoustic wave, or a continuous sine wave, may be generated to measure coating wear on both the blades and the vanes. A rapid sequence of pulses ensures that a pulse is present as a blade passes the vane. The measured magnitude of the acoustic waves at one vane will increase as a blade passes that vane due to the gas pressure, which will produce a regular pattern of increasing and decreasing magnitude in the acoustic waves as long as all blades are in good condition. As before, the magnitude and velocity of the acoustic wave will vary according to the condition and bond strength of the thermal barrier coating, and the strain to which the blade is subjected. As the coating on the blades deteriorates, the magnitude and/or velocity of the resulting acoustic wave will change, indicating that a blade needs servicing.

Alternatively, acoustic signals within the turbine can be monitored without the need for generating the acoustic signal. As each blade passes a vane, the blade will produce a gas pressure pulse and resulting acoustic wave at that vane. The acoustic waves are received by an acoustic waveguide. The acoustic waveguide will transmit the acoustic wave to an acoustic receiver for converting the acoustic signal to an electrical signal. The electrical signal will then be transmitted to a filter to remove the lower frequency signals of the turbine from the higher frequency signals to be analyzed. The signal is finally sent to a storage scope and computer, permitting the variations in the acoustic waves to be analyzed. A particular acoustic signal having increasing magnitude indicates a blade having a deteriorating coating.

It is therefore an aspect of the present invention to provide an apparatus for monitoring the condition of a component within a turbine while the turbine is operating.

It is another aspect of the present invention to provide an apparatus for monitoring the condition of a coating on a component within a turbine while the turbine is operating.

It is therefore a further aspect of the present invention to provide an apparatus for monitoring the condition of a thermal barrier coating on the components of a combustion turbine while the turbine is operating.

It is another aspect of the present invention to provide a method for monitoring the condition of a thermal barrier coating on the components of a combustion turbine while the turbine is operating.

It is a further aspect of the present invention to determine the status of a thermal barrier coating by passing an acoustic wave through that coating, and analyzing the acoustic wave for changes in magnitude.

A better understanding of the present invention can be obtained from the following description, with reference to the drawings.

BRIEF DESCRIPTION OF THE DRAWINGS

Like reference numerals denote like elements throughout the drawings.

DESCRIPTION OF THE PREFERRED EMBODIMENTS

The preferred embodiment of the invention is a system for online monitoring the condition of the vanes and blades within a combustion turbine. The system permits monitoring any condition resulting in changes to the acoustic properties of components within the combustion turbine, such as deterioration of the thermal barrier coating covering the blades and vanes. The significance and functioning of the present invention are best understood through a description of the environment within a combustion turbine.

Figure 1:
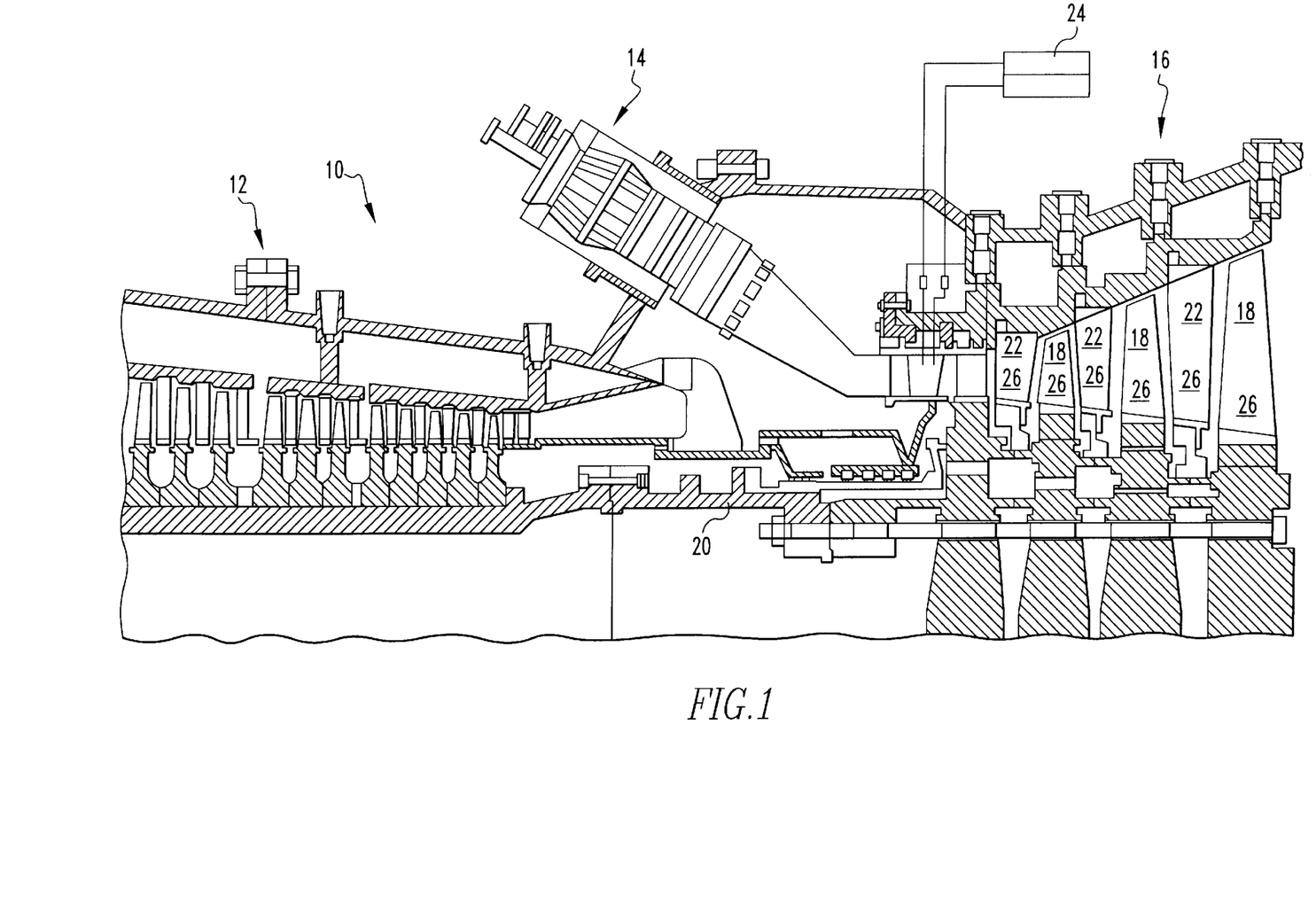
FIG. 1 is a cross sectional view of a combustion turbine for which the present invention will be used.

FIG. 1 illustrates a combustion turbine 10. The combustion turbine 10 includes a compressor 12, at least one combustor 14, and a turbine 16. The turbine 16 includes a plurality of rotating blades 18, secured to a rotatable central shaft 20. A plurality of stationary vanes 22 are positioned between the blades 18, with the vanes 22 being dimensioned and configured to guide air over the blades 18. The blades 18 and vanes will typically be made from nickel-cobalt, and will typically be coated with a thermal barrier coating 26, such as yttria-zirconia.

In use, air is drawn in through the compressor 12, where it is compressed and driven towards the combustor 14. The combustor 14 mixes the air with fuel and ignites it, thereby forming a working gas. This working gas will typically be approximately 2500° F. to 2900° F. (1371° C. to 1593° C.). This gas expands through the turbine 16, being guided across the blades 18 by the vanes 22. As the gas passes through the turbine 16, it rotates the blades 18 and shaft 20, thereby transmitting usable mechanical work through the shaft 20. The combustion turbine 10 also includes a cooling system 24, dimensioned and configured to supply a coolant, for example steam or compressed air, to the blades 18 and vanes 22.

From the above description, it becomes apparent that the environment wherein the vanes 22 and blades 24 operate is particularly harsh, resulting in serious deterioration of the blades 18 and vanes 22 if the thermal barrier coating 26 should deteriorate. Further, such an environment is likely to cause other forms of component deterioration, such as deterioration of coatings for corrosion prevention, or formation of cracks within the coatings, or the underlying components. Although the description below relies on the example of monitoring of thermal barrier coating deterioration within a combustion turbine, the same procedure may be used for online monitoring of any form of deterioration affecting the acoustic characteristics of the turbine, or possibly thermal barrier coatings used for other applications wherein pressure, stress, and/or friction are applied to the coated component.

Figure 2:
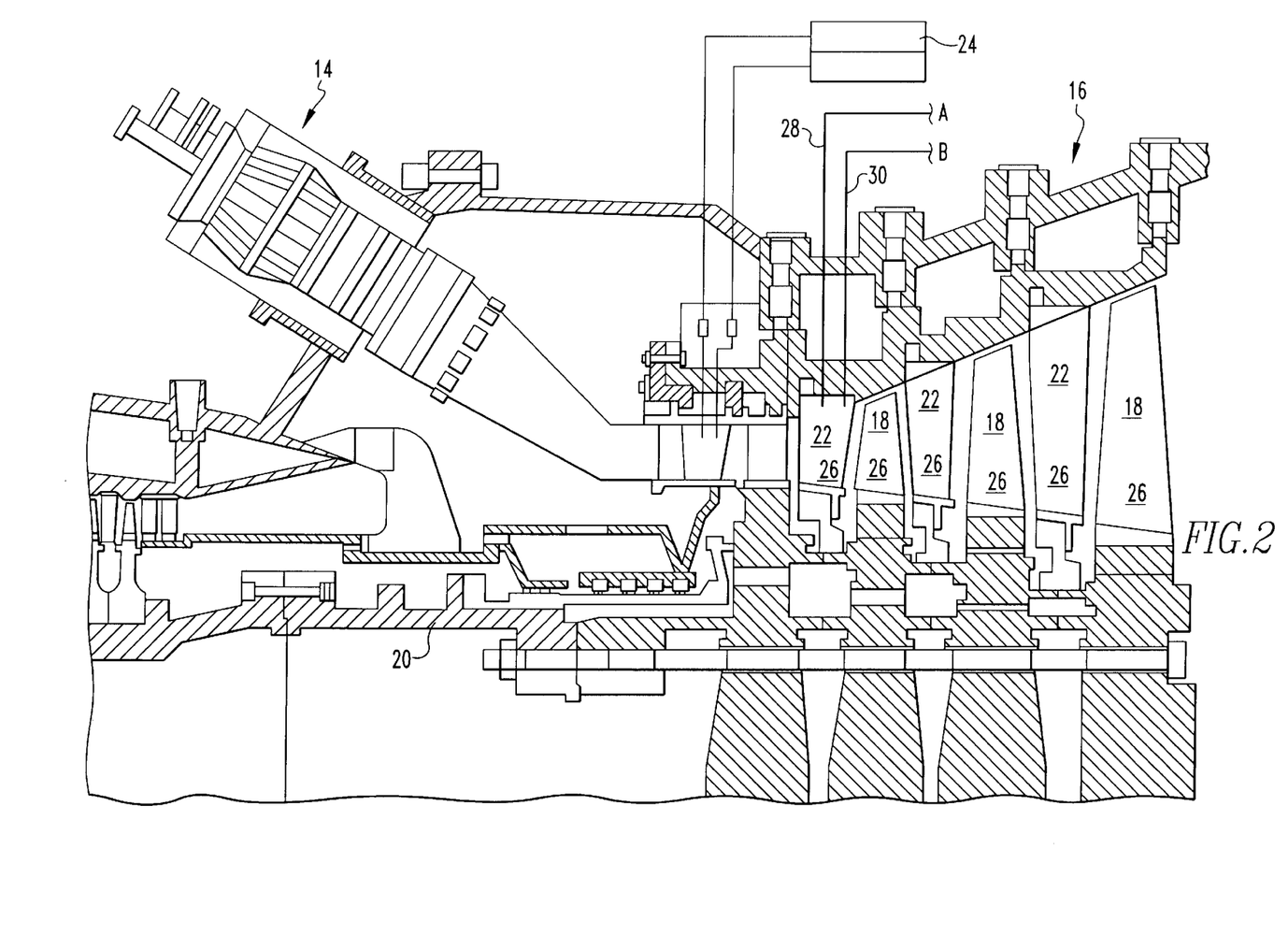
FIG. 2 is a cross sectional view of the turbine portion of a combustion turbine, illustrating the placement of the acoustic waveguides within the turbine, according to the present invention.
Figure 3:
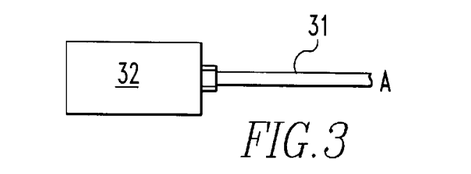
FIG. 3 is a schematic diagram of a pulse signal generator used according to the present invention.
Figure 4:
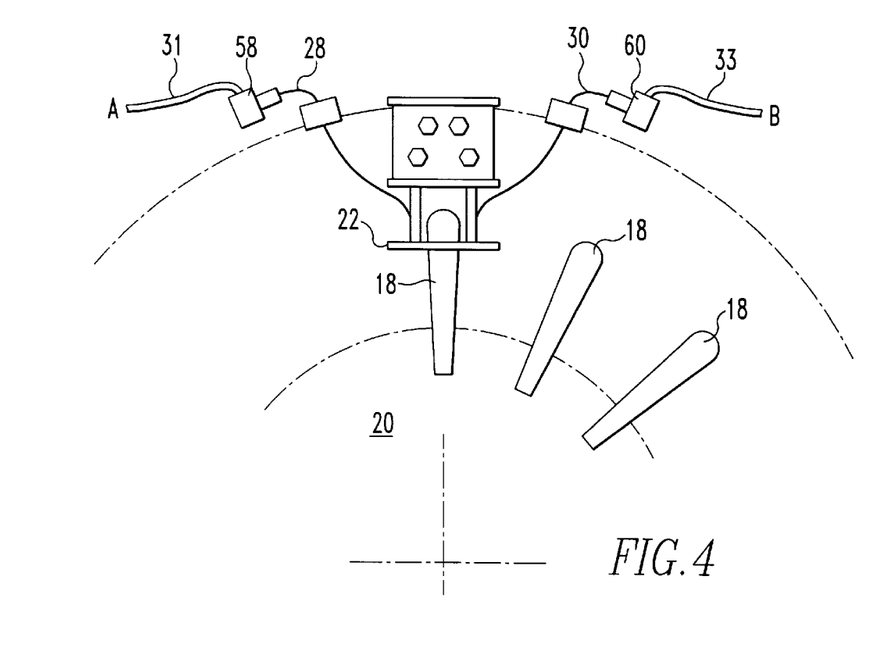
FIG. 4 is a schematic diagram of the turbine portion of a combustion turbine, illustrating the placement of the acoustic waveguides within the turbine, according to the present invention.
Figure 5:
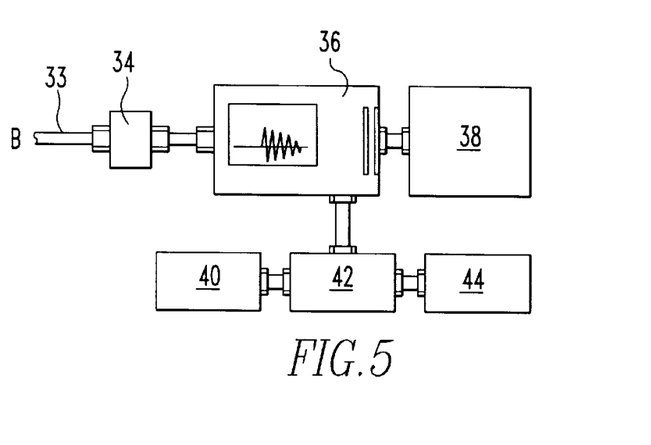
FIG. 5 is a schematic diagram of the apparatus used to store and analyze acoustic signals according to the present invention, including a filter, a storage scope, a computer, a spectrum analyzer, an acoustic emission counter, and a printer.

Although the monitoring system described herein will preferably be used with every vane 22 for which monitoring is desired within the turbine 16, which may be all vanes or only those vanes subjected to the highest temperatures and pressures, the system will be described herein using only a single vane 22. Referring to FIGS. 2 and 4, means for generating and receiving acoustic signals within the coating 26 (or within a component if other forms of deterioration are measured), which are preferably a pair of acoustic waveguides 28,30, are illustrated proximate to, and preferably secured to, a vane 22. A special feature of acoustic waveguides is that they can be bonded to vanes by either a point or direct contact or by bonding a few inches of acoustic waveguide length to the vane edges. In this way, either longitudinal waves or slow-moving surface waves can travel through the vane for interrogation. Referring to FIGS. 3–4, acoustic waveguide 28 is attached to an acoustic transmitter 58, which is attached to a pulse signal generator 32 by electrical lead 31. Referring to FIG. 5, acoustic waveguide 30 is attached to an acoustic receiver 60, which is attached to a filter 34 by electrical lead 33. A preferred filter is a high pass filter removing acoustic waves below 30 kHz. The filter 34 is attached to means for analyzing the acoustic signal to determine the existence and location of a defect within the coating. These components preferably include a storage scope 36 for measuring and storing information about the magnitude and velocity of the acoustic waves, computer 38 for analyzing the stored data, preferably using pattern recognition software, spectrum analyzer 40 for observing changes in the magnitude of acoustic waves at frequencies other than those generated by acoustic waveguide 28, acoustic emission counter 42 for detecting additional noise within the combustion turbine, as would be generated by a component approaching failure, and/or printer 44 for printing various collected data. Once the information is collected and stored, it may be analyzed as described below.

Depending on the type of monitoring desired, the pulse signal generator 32 may generate either a pulsed or a steady acoustic signal. Pulsed signals are useful for monitoring the coating 26 on the vanes 22. More rapidly pulsed signals, approximating a steady stream of pulses, are useful for monitoring the coating on the vanes 22 and blades 18. A sufficiently rapid, constant flow of pulses, preferably approximating a steady signal, ensures that a pulse will be present as a blade 18 passes the vane 22, permitting reliable monitoring of both the vane 22 and blades 18. A preferred and suggested acoustic wave will be 70 to 80 kHz., transmitted at 150 pulses per second in bursts of 32 Hz. Such an acoustic wave will permit monitoring of both blades and vanes.

To monitor the vanes during operation of the turbine, pulse signal generator 32 will generate a pulsed signal. The pulsed signal is transmitted to the acoustic transmitter 58, which is bonded to the acoustic waveguide 28, and may be a piezoceramic crystal, preferably resonant in the 70–80 kHz region. Acoustic waves from the acoustic transmitter 58 then travel through the acoustic waveguide 28, to the coating 26 of vane 22 as a high frequency acoustic wave. The acoustic wave travels through the coating 26 of the vane 22, before being received by the acoustic waveguide 30. The acoustic waveguide 30 will of course receive any acoustic waves within the turbine 16, in addition to the desired acoustic signals. The acoustic waveguide 30 then transmits the received acoustic waves to the acoustic receiver 60, which is preferably a piezoelectric crystal resonant in the 70–80 kHz region, converting the acoustic waves back to electrical pulses. This signal then passes through a filter 34 for removal of the low frequency acoustic signals generated through normal operation of the combustion turbine, leaving only the high frequency acoustic signal generated for interrogating the coating 26. The signal can then be measured and stored by the storage scope 36, analyzed using the computer 38, processed by the spectrum analyzer 40 and acoustic emission counter 42 to locate any other acoustic irregularities, and possibly printed using printer 44.

Figure 6:
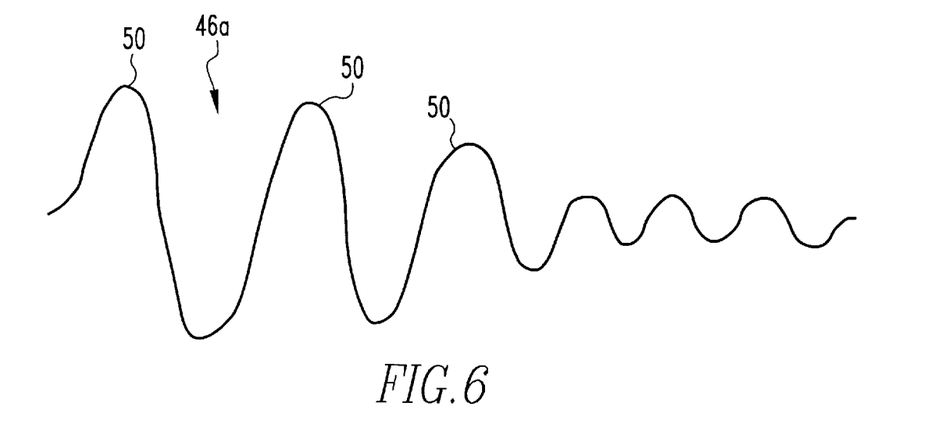
FIG. 6 is a schematic diagram of an acoustic signal pattern resulting from a pulsed signal, indicating an uncoated vane.
Figure 7:
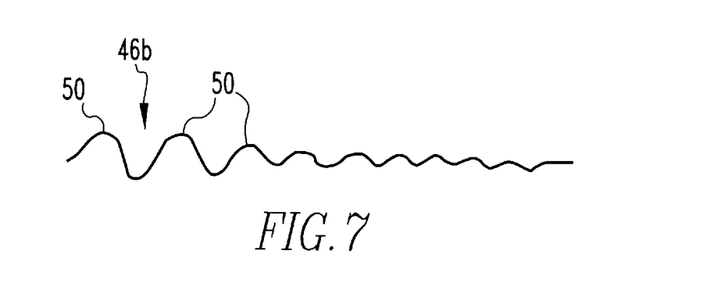
FIG. 7 is a schematic diagram of an acoustic signal pattern resulting from a pulsed signal, indicating an intact coating on a vane.

Using the above-described procedure, an acoustic wave passing through an uncoated vane is illustrated in FIG. 6, as sinusoidal display 46a. An acoustic wave passing through an intact coating 26 will have a significantly lower magnitude, as illustrated in FIG. 7, as sinusoidal display 46b having peaks 50. An acoustic wave passing through a partially deteriorated coating 26 will have a magnitude between that of sinusoidal display 46a and 46b, such as sinusoidal display 46c illustrated in FIG. 8. Therefore, increasing magnitude of the sinusoidal display indicates an increasing magnitude of the represented acoustic signal, indicating a deteriorating thermal barrier coating 26. In addition, it is anticipated that the wave velocity for an intact coating will be low, around 2500 m/sec, and will increase as the coating deteriorates to near 5,000 m/sec once the coating has totally deteriorated. The velocity is calculated from the time required for the acoustic wave to travel through the coating.

Alternatively, both blades 18 and vanes 22 may be monitored by using a constant acoustic wave. Pulse generator 32 generates a steady electronic signal, which is then converted to an acoustic wave by the acoustic transmitter 58, and transmitted by the acoustic waveguide 28 as a high frequency acoustic wave through the coating 26 of a vane 22. The acoustic waveguide 30 will receive the acoustic signal transmitted through coating 28, and will also receive another acoustic signal having a wide range of frequencies, created within the coating 26 of the vane 22 when a blade 18 passes the vane 22. The acoustic waveguide 30 will of course receive any acoustic waves within the turbine 16, in addition to the desired acoustic signals. The acoustic waveguide 30 then transmits the received signal to an acoustic receiver for converting the acoustic wave to an electronic signal. The electronic signal is then passed through a filter 34 for removal of the low frequency acoustic signals generated through normal operation of the combustion turbine, leaving only the high frequency acoustic signal generated by acoustic waveguide 28, and the high frequency portion of the acoustic signal from the pressure pulse of the blade 18 passing the vane 22. The signal can then be measured and stored by the storage scope 36, analyzed using the computer 38, processed by the spectrum analyzer 40 and acoustic emission counter 42 to locate any other acoustic irregularities, and possibly printed using printer 44.

Figure 8:
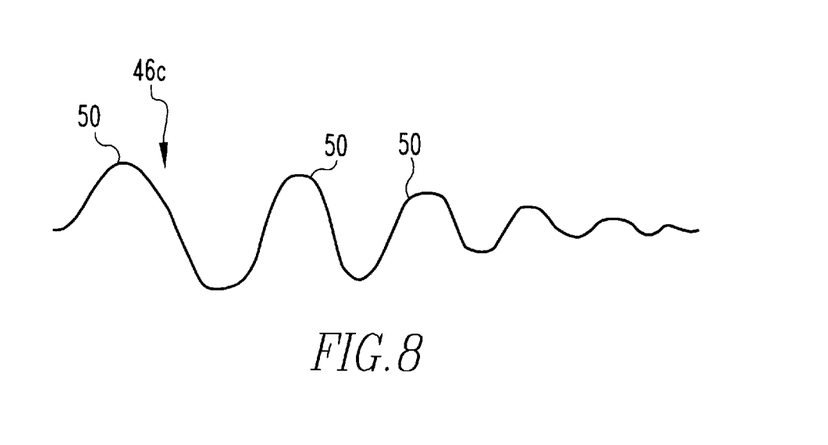
FIG. 8 is a schematic diagram of an acoustic signal pattern resulting from a pulsed signal, indicating a deteriorating coating on a vane.
Figure 9:
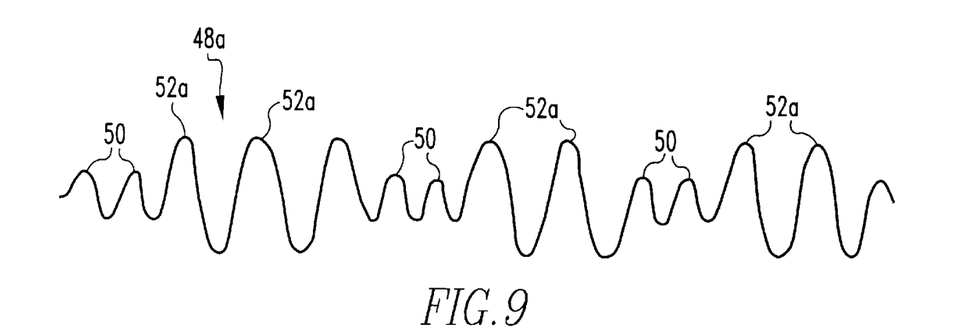
FIG. 9 is a schematic diagram of an acoustic signal pattern resulting from a constant signal, indicating an intact coating on a vane and on the blades passing the vane.
Figure 10:
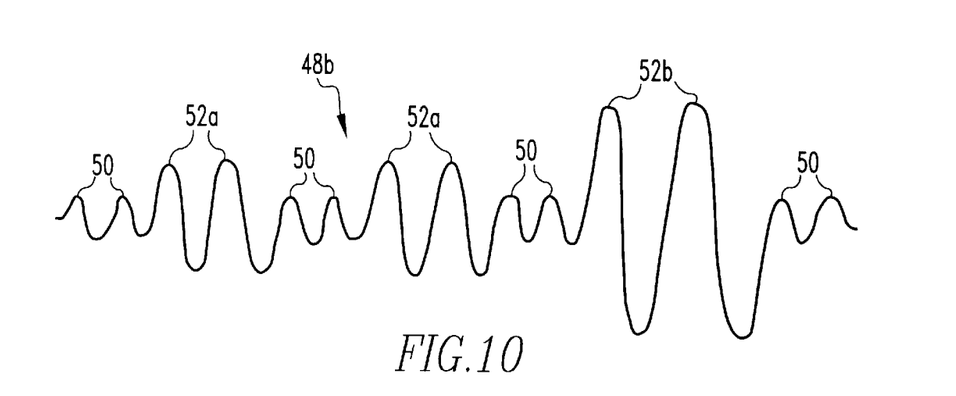
FIG. 10 is a schematic diagram of an acoustic signal pattern resulting from a constant signal, indicating an intact coating on a vane and a deteriorating coating on one blade passing the vane.
Figure 11:
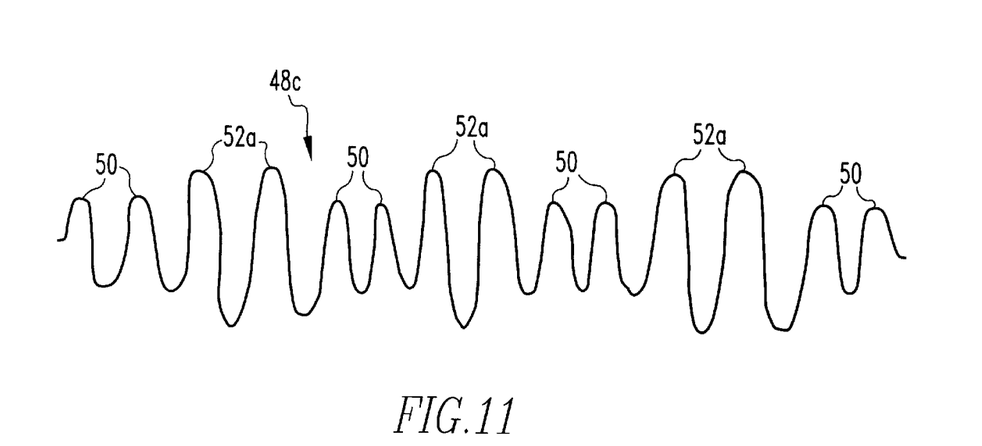
FIG. 11 is a schematic diagram of an acoustic signal pattern resulting from a constant signal, indicating a deteriorating coating on a vane and an intact coating on one blade passing the vane.

FIGS. 9–11 illustrate simulated sinusoidal displays 48a, 48b, 48c resulting from the above-described procedure. As illustrated in FIG. 9, the sinusoidal display 48a includes a series of smaller peaks 50, resulting from acoustic signals generated by the acoustic waveguide 28 only through the coating 26 of the vane 22. The peaks 50 in FIGS. 9–11 are therefore representative of the same acoustic signal (the acoustic wave passing through the vane without a pressure pulse from a blade) as the peaks 50 of FIGS. 6–8, with the only difference being that FIGS. 9–11 depict a constant stream of acoustic signals while FIGS. 6–8 illustrate individual acoustic signals having larger time intervals separating them from other signals. As the coating 26 of a vane deteriorates, the magnitude of the peaks 50 will increase in the same manner illustrated in FIGS. 6–8 and described above. The sinusoidal displays 48a,48b also include larger peaks 52a,52b, created by the pressure pulse created by a blade 18 passing a vane 22. FIG. 9 illustrates a sinusoidal display 48a, wherein all blades 18 and vanes 22 have intact coatings 26, and therefore all peaks 52a are the same height. FIG. 10 illustrates a sinusoidal display 48b, wherein all vanes 22 have intact coatings 26, but one blade 18 has a deteriorating coating 26, resulting in the peaks 52b having a larger magnitude than the peaks 52a. Such a situation should result in a sinusoidal display 48b for all vanes 22 associated with the blade 18 having the deteriorating coating 26, because that blade 18 will generate the same pressure pulse while passing all such vanes 22. FIG. 11 illustrates a sinusoidal display 48c, wherein the vane 22 to which the acoustic waveguides 28,30 in question are attached has a deteriorating coating 26, but all blades 18 have an intact coating 26, resulting in an increase in the magnitude of both peaks 50 and 52a. In such a case, examination of the sinusoidal displays associated with the other vanes 22 should resemble sinusoidal display 48a of FIG. 9, assuming that no other blade 18 or vane 22 has a deteriorating coating. It therefore becomes helpful to compare the various acoustic waves generated from a plurality of vanes 22 to more accurately locate a defect.

As a second alternative, the pulse generator 32 and acoustic waveguide 28 may be omitted, relying completely on the pressure pulse of a blade 18 passing a vane 22 to generate acoustic waves within the coating 26. The acoustic waveguide 30 will receive these acoustic signals, which will include a broad range of frequencies. The acoustic waveguide 30 will of course receive any acoustic waves within the turbine 16, in addition to the desired acoustic signals. The acoustic waveguide 30 then transmits the received signal through a filter 34 for removal of the low frequency acoustic signals generated through normal operation of the combustion turbine, leaving only those signals from the pressure pulse of the blade 18 passing the vane 22 that have frequencies exceeding the frequencies of the background noise. The signal can then be measured and stored by the storage scope 36, analyzed using the computer 38, processed by the spectrum analyzer 40 and acoustic emission counter 42 to locate any other acoustic irregularities, and possibly printed using printer 44.

Figure 12:
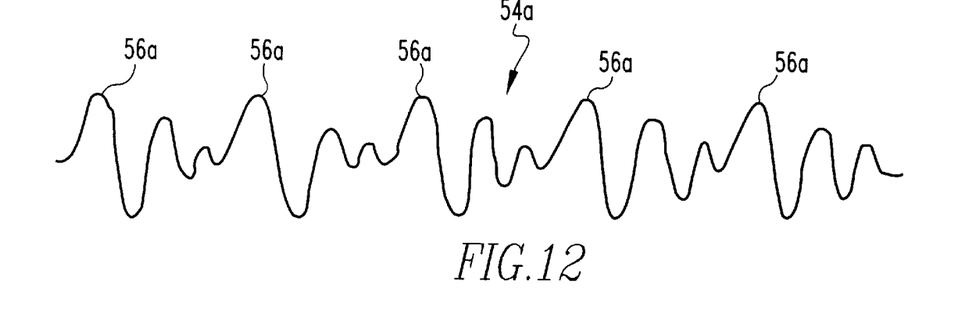
FIG. 12 is a schematic diagram of an acoustic signal pattern resulting from a series of pressure pulses applied to intact thermal barrier coatings.
Figure 13:
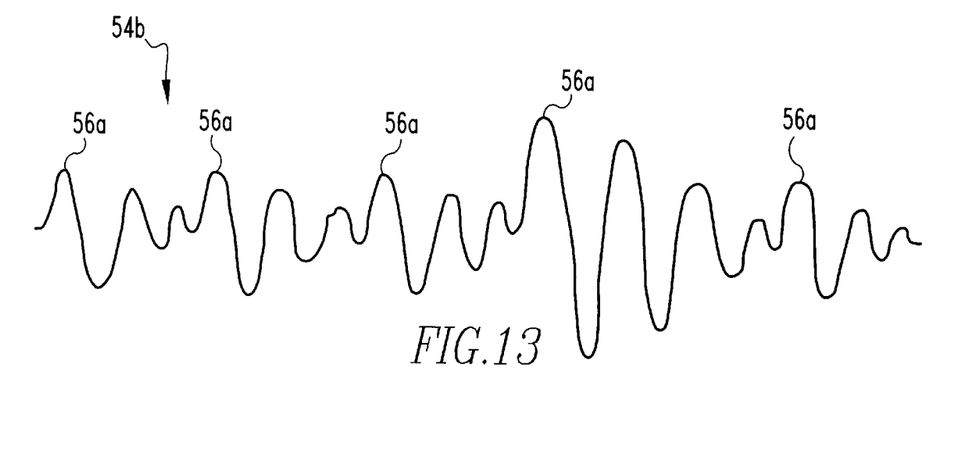
FIG. 13 is a schematic diagram of an acoustic signal pattern resulting from a series of pressure pulses applied to a vane having an intact coating by a blade having a deteriorating coating.
Figure 14:
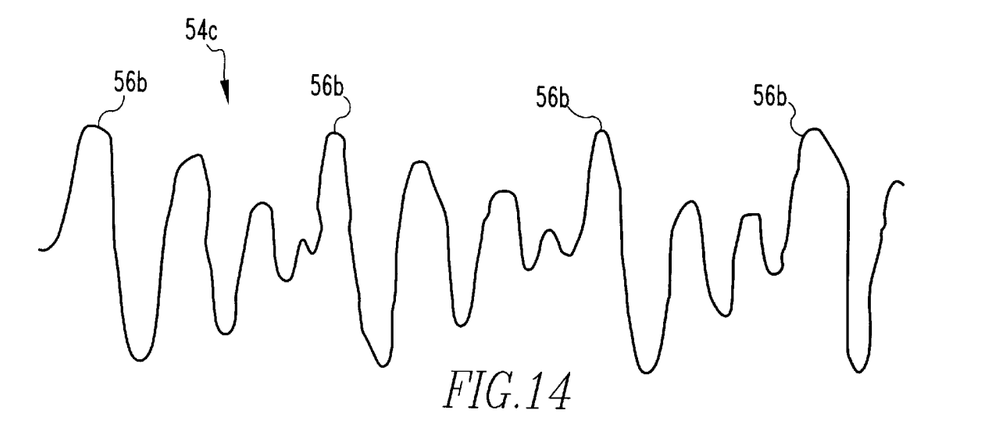
FIG. 14 is a schematic diagram of an acoustic signal pattern resulting from a series of pressure pulses applied to a vane having a deteriorating coating by a blade having an intact coating.

FIGS. 12–14 illustrate sinusoidal displays 54a,54b,54c representing the acoustic waves generated by the above-described pressure pulses. The peaks 56a increase in magnitude as a blade 18 passes the vane 22 to which the acoustic waveguide 30 is attached, then gradually decrease in magnitude as the vibrations dampen until the next blade 18 approaches the vane 22. The coating 26 will damp acoustic waves, so increasing magnitude of peaks indicates a deteriorating coating 26. FIG. 12 shows a sinusoidal display 54a indicating an intact coating on the vane 22 and all blades 18 passing the vane 22. Each pressure pulse creates a relatively low-magnitude, consistent peak 56a. FIG. 13 illustrates a sinusoidal display 54b, indicating that one blade 18 has a deteriorating coating 26. Most peaks 56a are consistent, but the peak 56b shows an increase in magnitude. Such a situation should result in a sinusoidal display 54b for all vanes 22 associated with the blade 18 having the deteriorating coating 26, because that blade 18 will generate the same pressure pulse while passing all such vanes 22. FIG. 14 illustrates a sinusoidal display indicating that the coating 26 of the vane 22 to which the acoustic waveguide 30 is attached is deteriorating. As the blades 18 pass this vane 22, all peaks 56b have increased magnitude. In such a case, examination of the sinusoidal displays associated with the other vanes 22 should resemble sinusoidal display 54a of FIG. 12, assuming that no other blade 18 or vane 22 has a deteriorating coating. It therefore becomes helpful to compare the various acoustic waves generated from a plurality of vanes 22 to more accurately locate a defect.

From the above description, it becomes apparent that, because there are many possible patterns of coating deterioration that may take place within a combustion turbine, there are many possible acoustic waves and resulting sinusoidal displays resulting from the monitoring system of the present invention. Each deteriorating component will influence the sinusoidal display as described above, and the combination of effects can be analyzed to determine which components need service. In the event that the resulting sinusoidal display proves difficult to analyze, the mere fact that there was a change of magnitude in the acoustic waves indicates that the turbine components require inspection and/or service.

While a specific embodiment of the invention has been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

We claim:

1. An apparatus for monitoring the condition of a component having a thermal barrier coating, said apparatus comprising:

an acoustic generator for generating an acoustic signal;

an acoustic receiver for receiving said acoustic signal;

a waveguide for guiding said acoustic signal from said acoustic generator to said component and from said component to said acoustic receiver, wherein a short section of said waveguide is bonded to a surface of said component to permit monitoring of surface waves in said component; and an analyzer connected to said acoustic receiver for analyzing said acoustic signal to determine the existence and location of a defect within said thermal barrier coating.

2. The apparatus according to claim 1, wherein said analyzer includes a filter for filtering out acoustic signals having a frequency below 30 kHz.

3. The apparatus according to claim 1, wherein said acoustic generator comprises a turbine blade passing a turbine vane to generate a pressure pulse.

4. An apparatus for monitoring the condition of a component within a combustion turbine, said apparatus comprising:

an acoustic generator for generating an acoustic signal;

an acoustic receiver for receiving said acoustic signal;

a waveguide for guiding said acoustic signal from said acoustic generator to said component and from said component to said acoustic receiver, wherein a short section of said waveguide is bonded to a surface of said component to permit monitoring of surface waves in said component; and an analyzer connected to said acoustic receiver for analyzing said acoustic signal to determine the existence and location of a defective within said component.

5. The apparatus according to claim 4, wherein said analyzer includes a filter for filtering out acoustic signals having a frequency below 30 kHz.

6. The apparatus according to claim 4, wherein said acoustic generator comprises a turbine blade passing a turbine vane to generate a pressure pulse.

* * * * *